(12) United States Patent
Vancamberg et al.

(10) Patent No.: US 11,701,075 B2
(45) Date of Patent: Jul. 18, 2023

(54) X-RAY IMAGE FEEDBACK FOR DXA SCAN FOV ADJUSTMENT

(71) Applicant: GE Precision Healthcare LLC, Wauwatosa, WI (US)

(72) Inventors: Laurence Vancamberg, Poissy (FR); Pablo Milioni de Carvalho, Chaville (FR); Serge Muller, Guyancourt (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 242 days.

(21) Appl. No.: 17/172,236

(22) Filed: Feb. 10, 2021

(65) Prior Publication Data

US 2022/0249045 A1 Aug. 11, 2022

(51) Int. Cl.
 *A61B 6/00* (2006.01)
 *A61B 6/04* (2006.01)
(52) U.S. Cl.
 CPC .......... *A61B 6/4452* (2013.01); *A61B 6/0407* (2013.01); *A61B 6/465* (2013.01); *A61B 6/505* (2013.01); *A61B 6/5211* (2013.01); *A61B 6/54* (2013.01)
(58) Field of Classification Search
 CPC ........ A61B 6/505; A61B 6/482; A61B 6/4509
 See application file for complete search history.

(56) References Cited

U.S. PATENT DOCUMENTS

| | | | |
|---|---|---|---|
| 6,081,582 A | 6/2000 | Mazess et al. | |
| 7,069,066 B2 | 6/2006 | Zeller et al. | |
| 7,174,000 B2 * | 2/2007 | Fehre | A61B 6/505 |
| | | | 378/54 |
| 7,995,822 B2 | 8/2011 | Lang et al. | |
| 9,642,585 B2 | 5/2017 | Wilson | |
| 10,390,784 B2 | 8/2019 | Wilson | |
| 10,499,873 B2 | 12/2019 | Wear et al. | |
| 10,699,405 B2 | 6/2020 | Payne et al. | |

(Continued)

FOREIGN PATENT DOCUMENTS

| | | |
|---|---|---|
| WO | 2014167097 | 10/2014 |
| WO | 2017212859 | 12/2017 |

OTHER PUBLICATIONS

Paudel, K., "Stitching of X-ray Images", Dissertation Uppsala Universitet, Nov. 2012, 78 pages.

(Continued)

*Primary Examiner* — Dani Fox
(74) *Attorney, Agent, or Firm* — Boyle Fredrickson, S.C.

(57) ABSTRACT

A system for performing a scan of internal structures of an object/patient is provided. The system includes a radiation source operative to emit a radiation beam, a radiation detector operative to receive the radiation beam and generate an output signal based at least in part on the received radiation beam, and a controller in electronic communication with the radiation source and the radiation detector and operative to generate at least one image of the object/patient. The controller is further operative to determine an offset of the at least one image relative to an image reference and to employ the offset to automatically align the at least one image with the image reference without the need for stopping the operation of the radiation source and detector to reposition the object/patient being scanned.

18 Claims, 7 Drawing Sheets

(56) References Cited

U.S. PATENT DOCUMENTS

2020/0029927 A1* 1/2020 Wilson ............... A61B 5/0077
2020/0046307 A1 2/2020 Wilson

OTHER PUBLICATIONS

Samsudin et al., "Development of Automated Image Stitching System for Radiographic Images", J. Digit. Imaging, Apr. 2013, 26(2):361-70.

Bondesson, D. et al., "Radiolucent Pressure Sensors For Mammography Applications", Masters Thesis, Lund University, Jun. 2014, 54 pages.

Fornvik, D. et al., "Pressure Distribution In Mammograph: compression of breats with malignant tumor masses", Medical Imaging 2013: Physics of Medical Imaging, Proc. of SPIE, vol. 8668, 86684E-1, 9 pages.

M. Dustler et al., "The Effect of Breast Positioning on Breast Compression in Mammography: a Pressure Distribution Perspective", Medical Imaging 2012: Physics of Medical Imaging. Proc. of SPIE, vol. 8313, 83134M, 7 pages.

* cited by examiner

X-RAY IMAGE FEEDBACK FOR DXA SCAN FOV ADJUSTMENT

FIELD OF THE DISCLOSURE

The present disclosure relates generally to dual-energy x-ray absorptiometry ("DEXA" or "DXA") systems and methods, and more specifically to modes of operation of those types of imaging systems.

BACKGROUND OF THE DISCLOSURE

Bone density imaging systems, such as dual-energy x-ray absorptiometry ("DEXA" or "DXA") systems and devices, among others, include an x-ray source that emits a collimated beam of dual-energy x-rays to image an object/patient. In such systems, an x-ray detector is positioned with respect to the x-ray source so as to receive the x-rays that have passed through the object. The x-ray source and the x-ray detector typically move in unison along a path that traverses the object during a scan, and the detectors of many such systems typically output/produce electrical signals in response to the received x-rays. In many bone density imaging systems, the electrical output signal of the detector is usually digitized and subsequently used by the bone density imaging system to generate scanned images of the object. Measurements of the x-ray absorption by the imaged object at two different x-ray energies reveals information about the composition and/or density of the object as decomposed into two selected basis materials, e.g., fat/soft tissue and bone.

Figure 1:
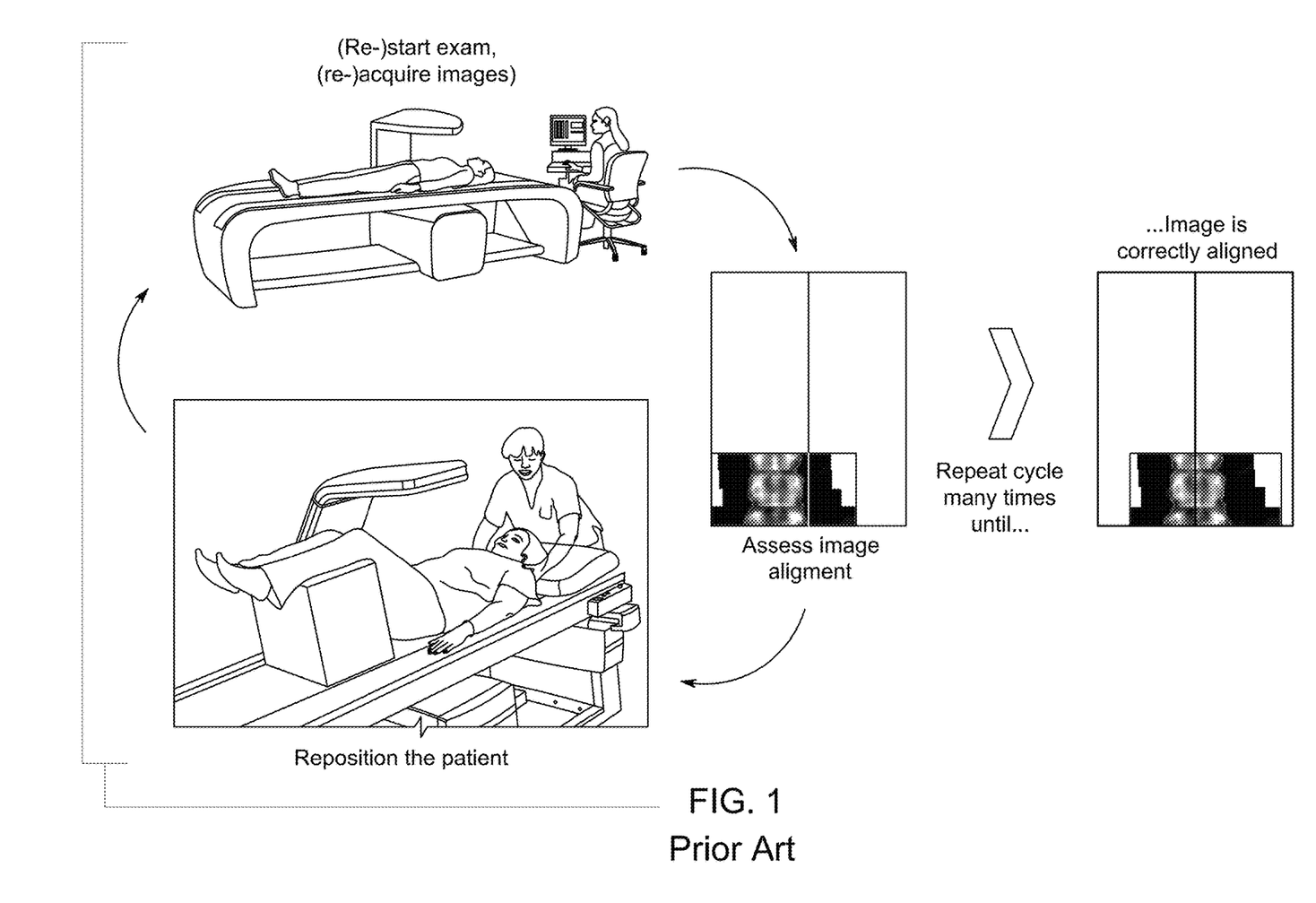
FIG. 1 is a schematic view of a method of aligning a patient with a prior art DXA imaging system.

In a DXA imaging procedure, as schematically shown in FIG. 1, the DXA system moves the arm and x-ray source along the portion of the body of the patient to be imaged in order to obtain multiple pairs (high and low energy) of two dimensional (2D) DXA images of the specified portion of the patient. The DXA system can move the x-ray source and x-ray detector along the body of the patient from head to toe or along any portion of the body in order to obtain the desired DXA images. Depending upon the type of beam generated by the x-ray source, e.g., pencil, fan or narrow fan, the x-ray source and/or detector can move directly along the main axis of the patient body or in a raster scan pattern in order to enable the x-ray source and detector to image the entire or specified portion of the body of the patient. In certain embodiments, the x-ray source and detector are operated to perform a scan along the entire imaging window of the DXA system, while in other embodiments the DXA system can operate the x-ray source and detector to perform scan of multiple individual sections or sweeps of the source and detector across the imaging window.

In the DXA imaging procedure, as illustrated in FIG. 1, upon initial operation of the DXA system, the operator reviews the initial image produced by the DXA system in order to determine the alignment of the image and thus the patient with regard to the imaging system. Proper alignment or centering of the field of view (FOV) of the image is essential to ensure that all areas of interest being scanned are represented in the DXA images.

If the images show that the patient and/or the portion of the patient being imaged are not aligned with the DXA system, such as with regard to a centerline of the imaging window for the DXA system, an image from a prior scan, and/or another best practice guideline for the images, the operator will abort or stop the DXA system in the case of a sweep imaging procedure and re-position the patient on the DXA system. The operator will then re-start the DXA system to obtain new images of the patient for a subsequent determination of the alignment of the patient with the DXA system. The operator will continue this process until the initial sweeps or images of the DXA scan show proper alignment of the patient/images with the DXA system.

This process enables the operator to ensure that the images created by the DXA system illustrate the desired portion(s) of the patient being scanned to provide the operator with the desired information regarding the internal bone structure of the patient. However, with the number of iterations of the scanning process required for the determination of the proper positioning of the patient to obtain the desired image alignment, the total amount of x-rays dosed to the patient and the time required for the performance of the entire imaging process are each not desirable.

Alternatively, other DXA devices and systems have been developed that operate to create images of individual sections of the patient, or sweeps. These DXA systems/devices operate to image a portion of the patient after each transverse sweep of the x-ray source and detector. The DXA system analyzes the image of the section to determine where the bone is present in the image to enable the DXA system to estimate where to begin exposing the patient to X-rays on the subsequent sweep to capture the bone in subsequent images/sweeps. However, while these improved DXA systems enable more focused application of the x-rays to the regions of interest in the patient, the improved imaging processes still do not guarantee that the target body part is correctly aligned in the final image consisting of each of the sweeps in agreement with best practices.

Thus, similarly to prior art DXA systems/devices, to accommodate for any misalignment, these improved DXA systems can provide initial sweeps of the patient for review by the operator for determination of the alignment of the patient on the DXA system/device, rather than having to perform a full scan as in prior art DXA systems and/or devices. However, even with the reduced time for making the alignment determination based on the ability to review the initial sweeps as opposed to the full image, to ascertain the proper alignment of the patient it is still required to iteratively halt the DXA system scan, re-position the patient on the DXA system/device and re-initiate the scan to have the regions of interest of the patient properly located within the scan images/sweeps.

As a result, it is desirable to develop an automated image alignment system for a DXA imaging system or device to eliminate or significantly reduce the iterative alignment process required in prior art DXA imaging systems.

SUMMARY OF THE DISCLOSURE

According to one aspect of an exemplary embodiment of the disclosure, an automated image alignment system is provided for a DXA imaging system. The automated imaging system is operable to review the initial scans or image sections obtained by the DXA imaging system and determine the alignment of the individual scans with regard to an alignment reference for the alignment system. If one or more of the scans are misaligned with regard to the alignment reference, the alignment system can adjust the operation of the x-ray source to correspond to the actual location of the patient on the DXA system/device, thereby aligning subsequent scans with the alignment reference for the alignment system.

According to still another aspect of an exemplary embodiment of the present disclosure, a DXA imaging system includes a support on which an object to be imaged is adapted to be positioned, a radiation source movably disposed relative to the support and configured to emit radiation beams towards the object, a detector movably disposed relative to the support and aligned with the radiation source to receive the radiation beams from the radiation source and generate image data, a controller operably connected to the radiation source and the detector to control the movement and operation of the radiation source and detector, the controller configured to receive and process image data from the detector to obtain at least one image of the object, a display operably connected to the controller for presenting information to a user, and a user interface operably connected to the controller to enable user input to the controller, wherein the controller is configured to determine an offset for the at least one image relative to an image reference and to align the at least one image with the image reference.

According to still another aspect of an exemplary embodiment of the present disclosure, a method for automatically aligning images obtained while performing a DXA imaging procedure of an object includes the steps of providing a DXA imaging system having a support on which an object to be imaged is adapted to be positioned, a radiation source movably disposed relative to the support and configured to emit radiation beams towards the object, a detector movably disposed relative to the support and aligned with the radiation source to receive the radiation beams from the radiation source and generate image data, a controller operably connected to the radiation source and the detector to control the movement and operation of the radiation source and detector, the controller configured to receive and process image data from the detector, a display operably connected to the controller for presenting information to a user, and a user interface operably connected to the controller to enable user input to the controller, positioning the object on the support, operating the radiation source and the detector to obtain at least one image of the object, determining an offset of the at least one image relative to an image reference, and aligning the at least one image with the image reference.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including." and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

In addition, it is important to note that multiple variations of the basic functions and components of the dual-energy x-ray absorptiometry ("DEXA" or "DXA") system and/or device described here exist, but while having different implementations, the functions and elements presented in the following manner regarding the disclosed DXA systems are intended to broadly cover other configurations and types of DXA systems, such as, but not limited to those disclosed in U.S. Pat. No. 10,499,873, entitled *System And Method For Performing A Bone Density Scan Of A Patient*, and U.S. Pat. No. 10,699,405, entitled *System And Method For DXA Tomo-Based Finite Element Analysis Of Bones*, whose disclosures, structures and method(s) of operation are each expressly incorporated herein by reference for all purposes. Further, while the embodiments disclosed herein are described with respect to dual-energy x-ray absorptiometry ("DEXA" or "DXA"), it is to be understood that embodiments of the present invention may be applicable to other types of medical imaging systems. Further still, as will be appreciated, embodiments of the present invention related imaging systems may be used to analyze tissue generally and are not limited to human tissue.

Referring now to FIG. 1, the major components of a system 10 for performing a scan of internal components of an object/patient 12, such as a bone density scan, are shown. As will be appreciated, in embodiments, the system 10 may be a DXA system that functions as a dual energy bone densitometer capable of performing bone densitometry. Accordingly, in embodiments, the bone density scan performed by the system 10 may be used to generate a bone mineral content ("BMC") measurement, a bone mineral density ("BMD") measurement, body composition measurement, an atypical femur fracture ("AFF") measurement, and/or a body thickness measurement. In embodiments, the BMD may be calculated by dividing the BMC by the area of bone imaged. During operation of the system 10, in accordance with embodiments of the invention, an x-ray beam with broadband energy levels is utilized to scan the object/patient 12 to image internal structures of the object/patient 12, e.g., the patient's bones. The acquired scanned images may then be used to diagnose a medical condition such as osteoporosis. In embodiments, the scanned images may be generated in part from determined bone density information acquired during a dual-energy x-ray scan.

Figure 2:
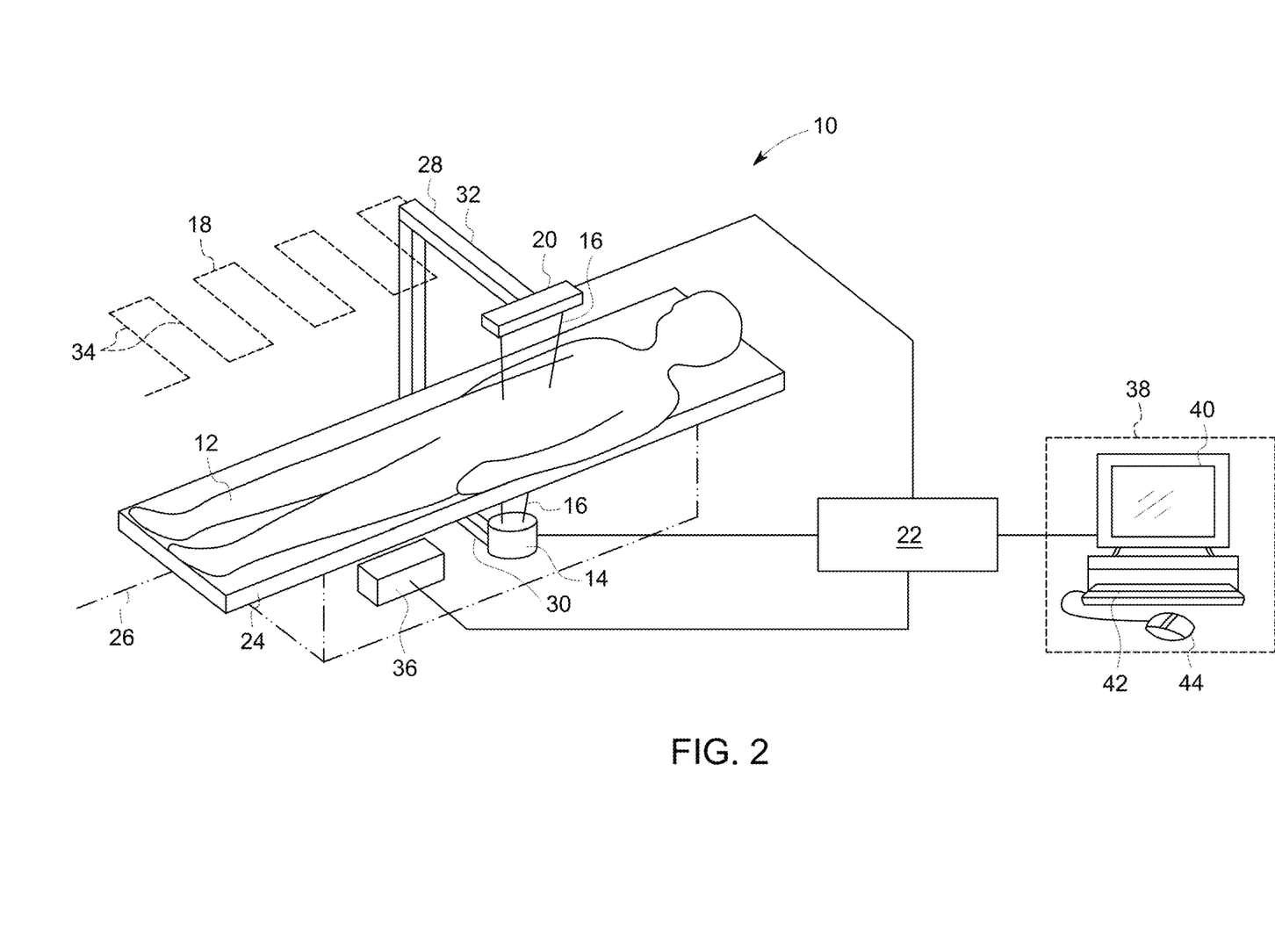
FIG. 2 is a perspective view of a DXA system for performing a bone density scan of a patient in accordance with an exemplary embodiment of the disclosure.

Accordingly, and as shown in FIG. 2, the system 10 includes an x-ray or radiation source 14 operative to emit an x-ray or radiation beam 16 and to move along a scanning path 18, a radiation detector 20 operative to move along the scanning path 18 and to receive the radiation beam 16, and a controller 22 in electronic communication with the radiation source 14 and the radiation detector 20. As will be described in greater detail below, the controller 22 is operative to regulate the radiation beam 16 while the radiation source 14 and the radiation detector 20 move along the scanning path 18 such that a flux of the radiation beam 16 at the radiation detector 20 is within a target flux range.

In exemplary embodiments, the system 10 may further include a support/patient table 24 for providing a horizontal surface for supporting the object/patient 12 in a supine or lateral position along a longitudinal axis 26, a support member 28, which in embodiments, may be a C-arm having a lower end 30 and an upper end 32, the lower end 30 being positioned beneath the table 24 so as to support the radiation source 14, and the upper end 32 positioned above the table 24 so as to support the radiation detector 20. While the radiation source 14 and the radiation detector 20 are shown in FIG. 1 as being below and above the patient 12, respectively, it will be understood that the positions of the radiation source 14 and the radiation detector 20 may be reversed such that the radiation source 14 and the radiation detector 20 are above and below the patient 12, respectively. In embodiments, the radiation detector 20 may be fabricated, for example, as a multi-element cadmium-tellurium ("CdTe") detector that provides for energy discrimination. In embodiment, the radiation detector 20 may also be a single or multi-element scintillator with photomultiplication for energy discrimination.

As stated above, the radiation source 14 and the radiation detector 20 move along the scanning path 18 so as to trace a series of transverse scans 34 of the patient 12, during which dual energy radiation, e.g., x-ray, data is collected by the radiation detector 20. In embodiments, the transverse scanning procedure generates either a single scan image or a quantitative data set from a plurality of scanned images acquired across the patient 12, wherein the radiation source 14 and the radiation detector 20 are either longitudinally aligned with the superior-inferior axis of the patient 12 or transversely from one side of patient to another, e.g., left to right. As will be appreciated, scanning the patient 12 using a transverse motion facilitates minimizing the time between acquisitions of adjacent scanned images since the transverse direction across the patient 12 is shorter than the longitudinal direction across the patient 12. Thus, transverse scanning may reduce the severity of motion artifacts between the scanned images, which in turn may further provide for improved accuracy in merging acquired scanned images. As will be appreciated, however, in embodiments, the scanning path 18 may be a series of longitudinal scans.

In certain embodiments, the transverse scanning motion may be produced by actuators (not shown) controlled via a translation controller 36 which may be in electronic communication with, or form part of, the controller 22. During operation, the radiation source 14 produces/generates/emits the radiation beam 16, which in embodiments, may have a fan shape having a plane that is parallel to the longitudinal axis 26. In other embodiments, however, the radiation beam 16 may have a fan shape having a plane that is perpendicular to the longitudinal axis 26. Further, in embodiments, the scanning pattern/path 18 may be configured such that there is some overlap (e.g., 10% of the scanned surface area) between successive scan lines 34 of the radiation beam 16. As will be understood, in embodiments, the radiation beam 16 may have a pencil shape, a fan shape, a cone shape, and/or other shapes appropriate for scanning the patient 12.

In embodiments, the radiation source 14, the radiation detector 20, and the translation controller 36 may be controlled via the controller 22. The controller 22 may electronically communicate with a terminal 38 that includes a display 40, a keyboard 42, and a cursor control device 44, e.g., a mouse, that provide for the input and output of information, e.g., text, images, and/or other forms of data, into and out of the system 10. In embodiments, the controller 22 may be located remotely from the terminal 38. In other embodiments, the controller 22 may be integrated into the terminal 38. In embodiments, the controller 22 is adapted to perform one or more processing operations. For example, the bone and tissue information acquired by the radiation detector 20 may be processed and displayed in real-time during a scanning session as the data is received by the controller 22 from the radiation detector 20. The display 40 may include one or more monitors that present information concerning the patient 12, e.g., the scanned images and bone length images, to the operator for diagnosis and analysis. The displayed images may be modified and the display settings of the display 40 also manually adjusted using the keyboard 42, the mouse 44, and/or a touch screen icon on the display 40.

As will be further understood, the system 10 may be configured to operate in a dual energy mode, a single energy mode, or a broadband mode. In single energy mode, the radiation beam 16 includes a single narrow band of energies, e.g., 20-150 keV. The single energy mode may provide for high resolution scanned images. In dual energy mode, the radiation beam 16 includes two or more narrow bands of energies, which may be emitted simultaneously or in succession. Dual energy mode may be utilized to acquire a scan image of the entire body of the patient 12 that includes information relating to the bones and tissues of the patient's 12 body, which in turn may be utilized to measure bone density and/or other bone and tissue characteristics or content. In broadband mode, the radiation beam 16 may include a single broad band of energies. As will be appreciated, the system 10 may be switchable between the various aforementioned modes.

Figure 3:
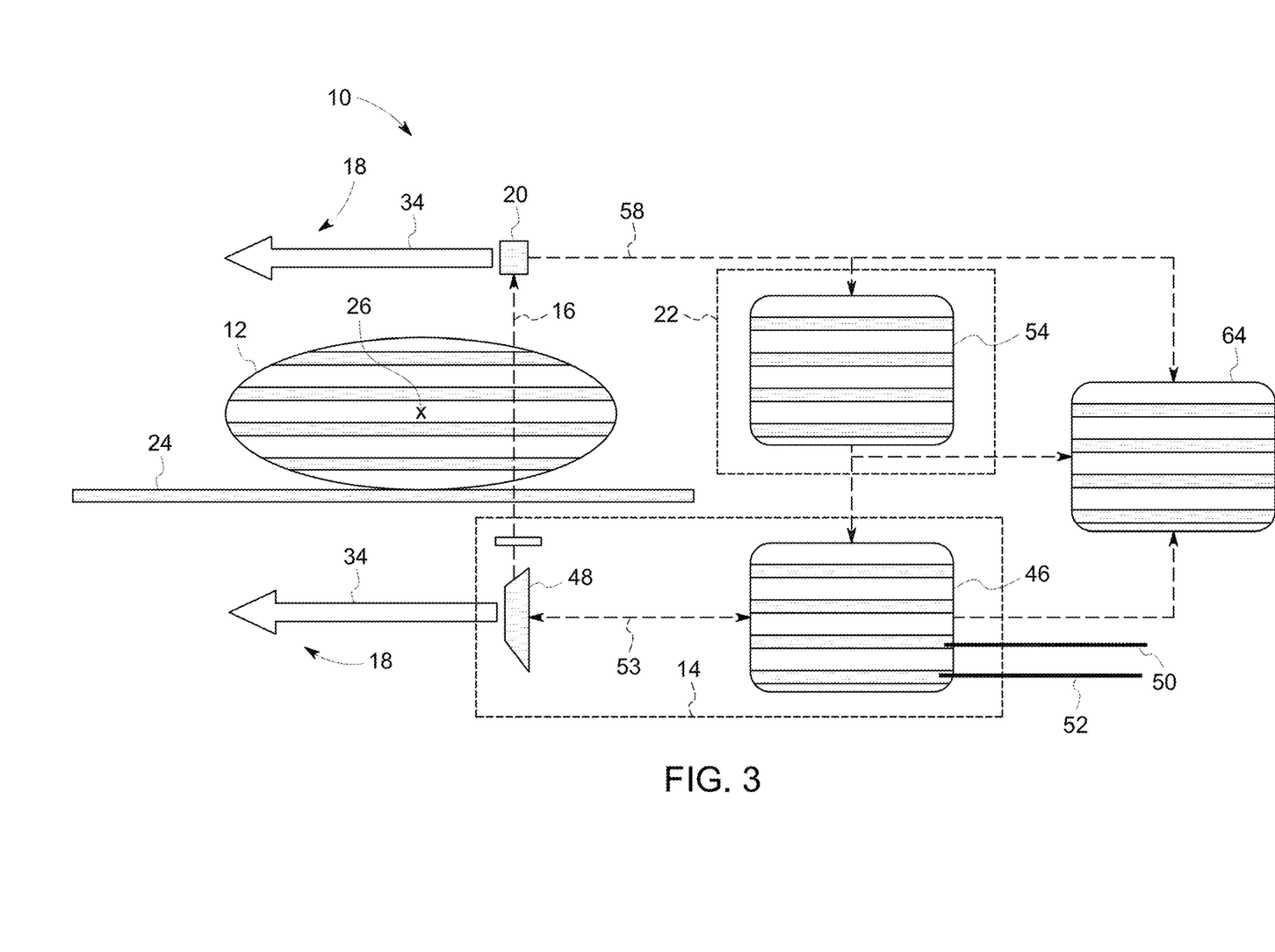
FIG. 3 is a block diagram of the DXA system of FIG. 2 in accordance with an exemplary embodiment of the disclosure.

Turning now to FIG. 3, a block diagram of the system 10 is shown wherein the longitudinal axis 26 is depicted as extending out of the drawing sheet, e.g., FIG. 3, depicts a longitudinal view of the patient 12 laying down on the table 24. As shown in FIG. 3, in embodiments, the radiation source 14 may include an x-ray or ray generator 46, an x-ray or ray tube 48, a source current 50, and a source voltage 52. As such, in embodiments, the ray generator 46 produces/generates an electrical current based on the source current 50 and/or the source voltage 52. The generated electrical current is then fed to the ray tube 48, via an electrical connection 53, which produces the radiation beam 16. As will be appreciated, the intensity of the radiation beam 16 at the ray tube 48 is at least partially determined by the source current 50 and the source voltage 52. As such, in embodiments, the initial setting(s) of the source current 50 and/or the source voltage 52 may be based on one or more characteristics of the patient 12, e.g., height, weight, body mass index, and/or other appropriate characteristics. For example, in some embodiments, the initial settings of the source current 50 and/or the source voltage 52 may be based at least in part on a height-and-weight chart that correlates various heights and weights to initial settings for the source current 50 and/or the source voltage 52. As will be appreciated, in embodiments, the initial source current 50 may be between about 0.1 mA to 3 mA.

As will be understood, as the beam 16 moves along the scanning path, the flux at the radiation detector 20 changes. For example, in embodiments, when the beam 16 is fully to the right or to the left of the patient 12 such that the beam 16 does not pass through the patient 12, i.e., when the beam 16 is "scanning in air," the intensity of the beam 16 at the detector 20, i.e., the flux, is substantially the same as the intensity of the beam 16 at the tube 48. In other words, the patient's 12 body is not absorbing and/or deflecting rays/photons from the beam 16. As the beam 16 begins to move across the patient 12, e.g., right to left, some of the rays/photons within the beam 16 are either absorbed and/or deflected by the patient's 12 body such that the intensity of the beam 16 at the detector 20, e.g., the flux, is less than the intensity of the beam 16 at the tube 48. As the beam 16 continues to cross the patient 12, the flux of the beam 16 at the detector 20 varies as the thickness and the density of the patient's 12 body varies.

As stated above, in embodiments, the controller 22 regulates the radiation beam 16 while the radiation source 14 and the radiation detector 20 move along the scanning path 18 such that the flux, i.e., the intensity of the beam 16 at the detector 20, is within a target flux range. As will be appreciated, in embodiments, the controller 22 may regulate the beam 16 in real-time and/or the target flux range may be between about 20-100.000 counts/s. As used herein, the term "count" means the detection of a photon by the radiation detector 20, e.g., 100 counts/s means that the radiation detector 20 detected 100 photons from the radiation beam 16 over a duration of time lasting one (1) second. Further, a data storage device/recorder 64 is in electronic communication with the controller 22 and operative to store data sent from the detector 20, operative commands for the operation of the system 10, and other relevant information for the operation of the system 10.

As further shown in FIG. 3, the controller 22 may include a flux converter 54 that adjusts the intensity of the beam 16 based on an output signal 58 of the detector 20. In other words, in embodiments, the flux converter 54 converts the output signal 58 into a desired beam 16 intensity at the tube 48 based on a desired flux at the radiation detector 20. In embodiments, the flux converter 54 may adjust the intensity of the beam 16 via adjusting the source current 50 and/or the source voltage 52. For example, if the controller 22 determines that the flux at the detector 20 is too high, e.g., greater than or equal to 100,000 counts/s, the flux converter 54 may lower either the source current 50 and/or the source voltage 52. Conversely, if the controller 22 determines that the flux at the detector 20 is too low, e.g., less than or equal to 20 counts/s, the flux converter 54 may increase either the source current 50 and/or the source voltage 52.

As will be understood, in embodiments, the output signal 58 generated by the radiation detector 20 may be a voltage and/or current, to include both direct current ("DC") and alternating current ("AC"), signal modulated by the radiation detector 20 in response to the amount of flux of the beam 16 as measured/sensed by the radiation detector 20. A such, in embodiments, the output signal 58 may be an analogue or a digital signal that encodes the level of flux of the beam as measured/determined by the radiation detector 20. For example, in embodiments, the output signal 58 may encode the flux of the beam 16 at the radiation detector as a range between about 0.95 mA to 1.0 mA.

Figure 4:
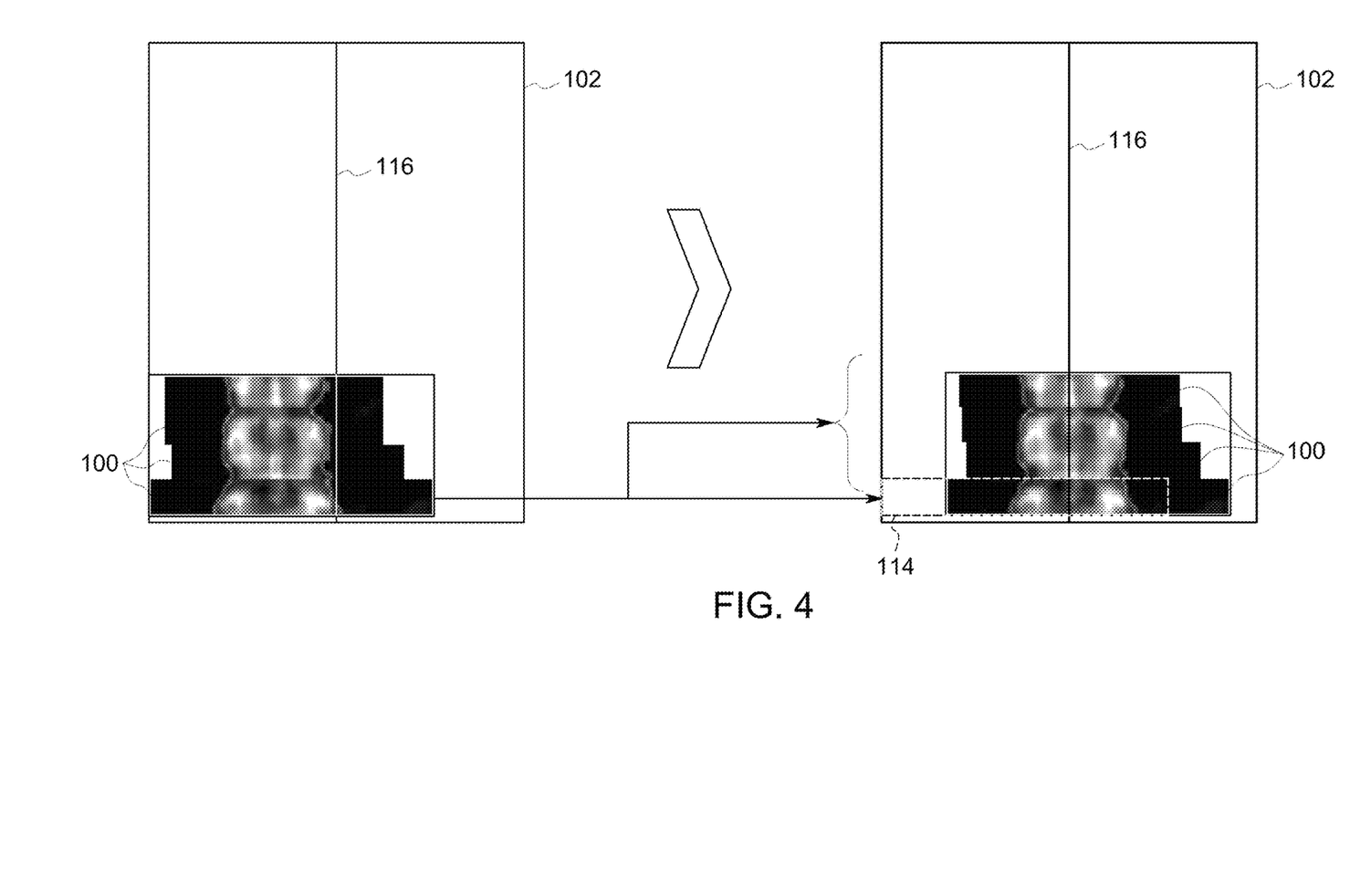
FIG. 4 is a schematic view of operation of the image alignment system operated with the DXA system of FIG. 2 to align images obtained by the DXA imaging system with an alignment reference in accordance with an exemplary embodiment of the disclosure.

Looking now at FIG. 4, when the DXA system 10 is operated to scan the patient 12, as described previously the radiation source 14 is operated as it moves along the defined path relative to the patient 12 to emit beams 16 that pass through the patient 12 and contact the detector 20. The information obtained from the beams 16 as they contact the detector 20 is utilized by the controller 22 to generate images 100 of the area(s) of the patient 12 scanned by the beams 16 in a known manner. After each pass, scan or sweep of the radiation source 14 across the patient 12, the controller 22 will generate the sweep image 100 for representation on the display 40. In generating the sweep image 100, the controller 22 will analyze the sweep image 100 in order to determine the location or representation of the bone within the sweep image 100. Using this location or position for the bone in the sweep image 100, the controller 22 can adapt the operation of the radiation source 14 to limit the emission of beams 16 from the source 14 to areas directly below and adjacent to the bone structure of the patient 12 to be imaged in order to produce relevant image data on the detector 20 without undue exposure of the patient 12 to beams 16 from the source 14 across the entire field of view (FOV) 102 of the DXA system 10.

As the sweep image(s) 100 is produced by the controller 22 in real time to enable the adaptation of the operation of the source 14 for successive sweeps during the scan being performed, the controller 22 will also present a representation of each sweep image 100 on the display 40 for the DXA system 10. The controller 22 can additionally locate the position of the sweep image 100 with respect to the FOV 102, such that the controller 22 of the DXA system 10 can determine the alignment of the sweep image 100 relative to the FOV 102, such as by determining the alignment of the anatomical structure contained in sweep image 100 relative to the FOV 102.

Figure 5:
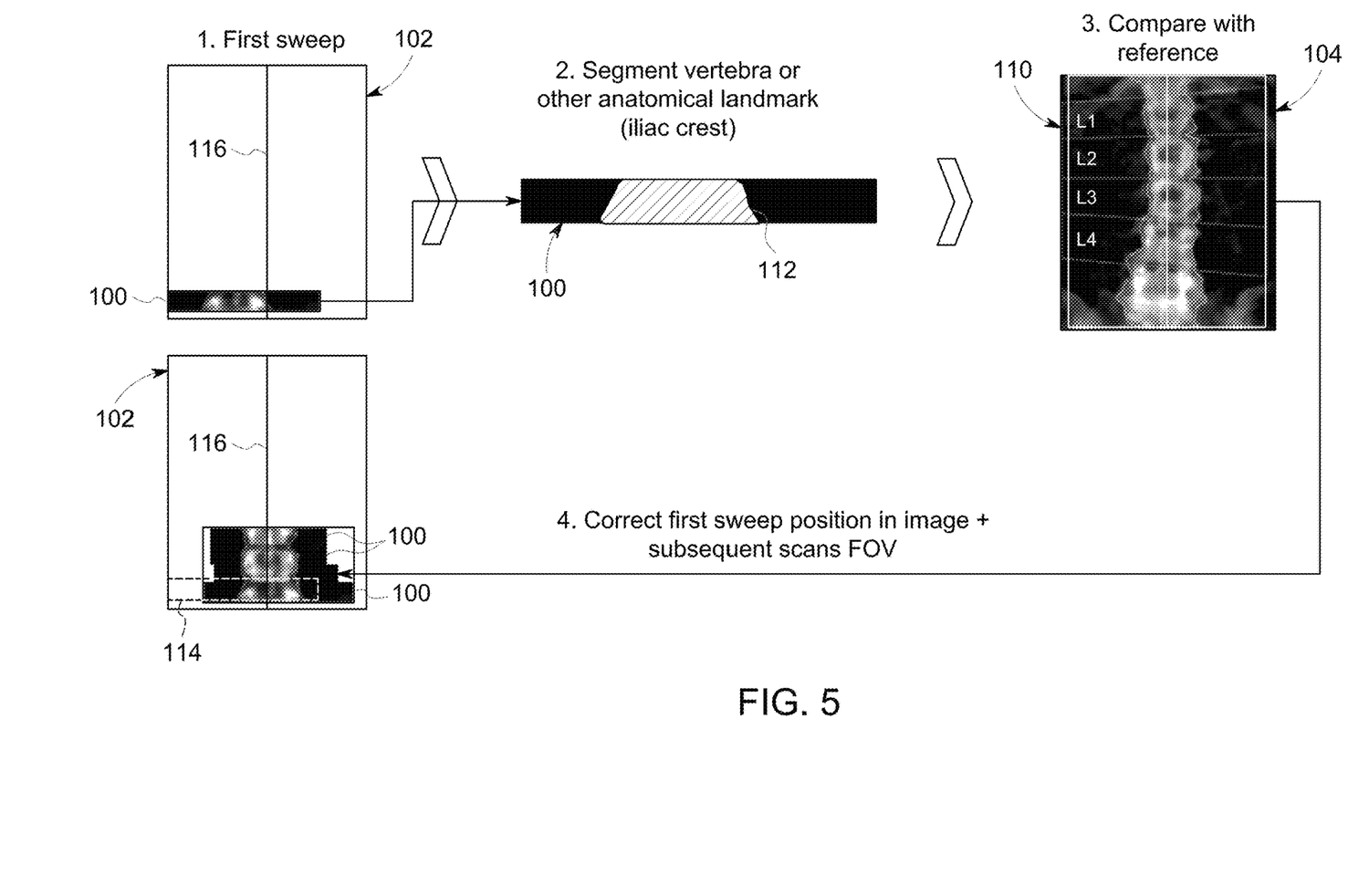
FIG. 5 is a schematic view illustrating an exemplary embodiment of the operation of the image alignment system of FIG. 4 in accordance with an exemplary embodiment of the disclosure.
Figure 6:
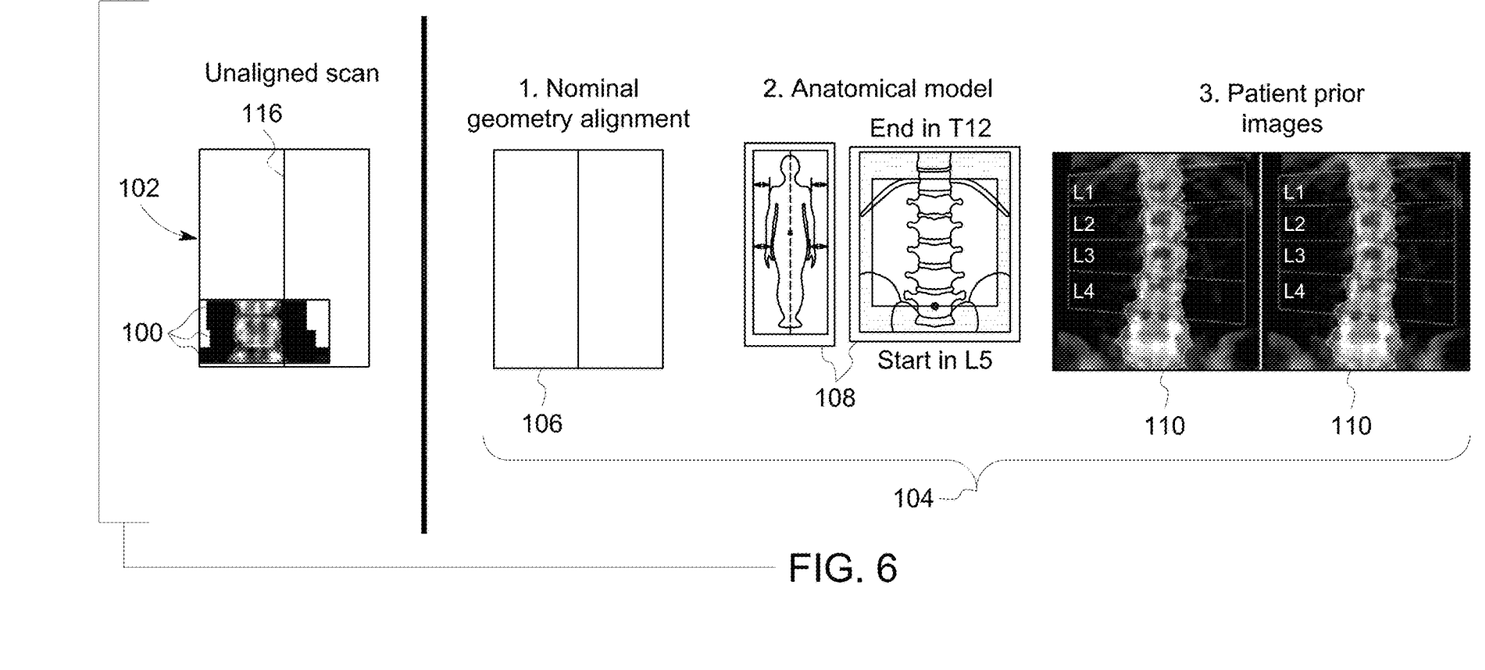
FIG. 6 is a schematic view of various alignment references that can be utilized by the image alignment system of FIG. 4 in accordance with an exemplary embodiment of the disclosure.

In one exemplary embodiment of the disclosure, the controller 22 initially compares the first sweep image 100, or any other number of initial sweep images 100, with an image reference 104 (FIG. 5) in order to determine if the sweep image(s) 100 is misaligned with the FOV 102, such as due to improper positioning of the patient 12 on the DXA system 10, e.g., the table 24. As shown in FIGS. 5 and 6, the image reference 104 can take a number of different forms, such as a geometric representation 106 of the FOV 102, a representative anatomical model 108 of the of the body of the patient 12, or prior scan images 110 of the patient 12, each of which are properly aligned with the FOV 102, e.g., with the centerline 116 of the FOV 102, for the DXA system 10.

Regardless of the form of the image reference 104, in the operation of the DXA system 10 to perform the image alignment, initially the controller 22 compares the position of the initial sweep image(s) 100 to the image reference 104. Should the sweep image 100 be determined to be misaligned with respect to the image reference 104, the controller 22 determines the difference in the actual position of the sweep image(s) 100 from the expected or aligned position relative to the image reference 104, optionally in real time as the initial sweep image(s) 100 is obtained. This process can be performed automatically by the controller 22, without the need for pausing and/or aborting the scan in progress, repositioning the object/patient 12 on the support/table 24, and restarting the scan, as in prior art systems and methods.

As shown in FIG. 5, in one exemplary embodiment, the determination of the difference in the actual position of the sweep image(s) 100 and the aligned position can be ascertained by the location of a structural and/or anatomical landmark 112 of the object/patient 12, such as the iliac crest, in the sweep image(s) 100 that is compared with the location or position of the same landmark 112 present in a prior scan image 110 of the patient 12. Using the difference in the locations of the landmark 112 in the sweep image(s) 100 and the prior scan image 110, where the prior scan image 110 has previously been aligned with the FOV 102 of the DXA system 10, the controller 22 can determine an offset 114 in the position of the patient 12 relative to the centerline 116 of the FOV 102 of the DXA system 10 due to improper positioning of the patient 12. Once the offset 114 is determined, the controller 22 can shift the position of the sweep image(s) 100 relative to the FOV 102 in order to align the sweep image(s) 100 on the centerline 116.

In one alternative embodiment, employed either alone or in combination with other embodiments, the offset 114 can be determined by the controller 22 using a comparison of landmarks 112 in the sweep image(s) 100 to other image references 104, such as the representative anatomical model/generalized representation 108 of the of the body of the patient 12. In another alternative embodiment, employed either alone or in combination with other embodiments, the offset 114 can be determined by comparing the information concerning the portion of the FOV 102 over which the source 104 was in operation to obtain the sweep image(s) 100 with the known position of the FOV 102, such as through the use of the geometric representation 106 of the FOV 102.

Further, with the offset 114 for the location of the sweep image(s) 100 known, the controller 22 can utilized the offset 114 to correct all subsequent sweep images 100 to properly align the sweep images 100 with the FOV 102. In one embodiment, the controller 22 can shift the position of each successively obtained sweep image 100 by the offset 114, either in real time as each sweep image 100 is obtained or after all of the sweep images 100 have been obtained. Alternatively, the controller 22 can shift the operation of the source 104 relative to the FOV 102 by the amount of the offset 104 to shift the location of the sweep image(s) 100 into alignment with the FOV 102.

In another exemplary embodiment, where the position of the patient 12 relative to the FOV 102 is determined using the image reference 104 to place the desired area of the patient 12 to be imaged completely outside of the FOV 102, the controller 22 can operate to automatically abort the scanning process, and optionally to provide a suitable indication to the operator of the positioning issue.

Figure 7:
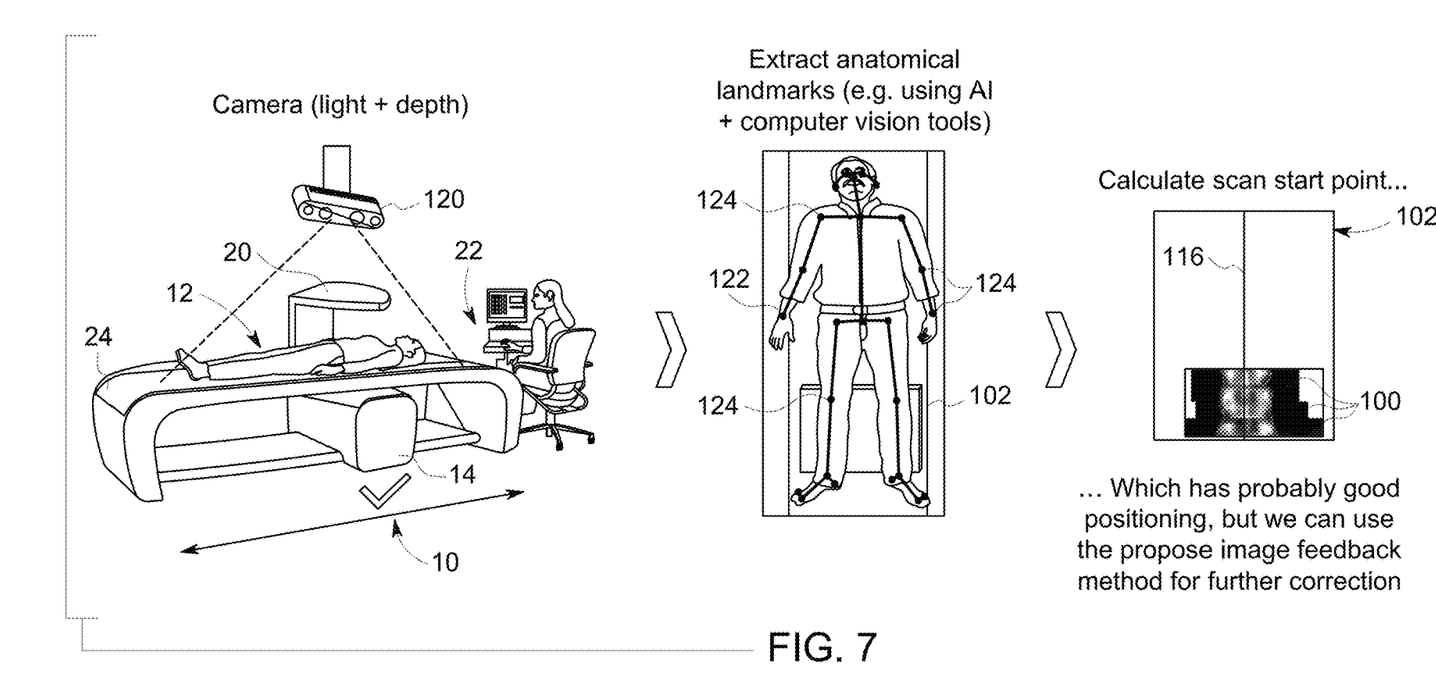
FIG. 7 is a schematic view illustrating another exemplary embodiment of the image alignment system of FIG. 4 in accordance with an exemplary embodiment of the disclosure.

Referring now to FIG. 7, in another exemplary embodiment of the disclosure, the DXA system 10 includes an optical camera 120 disposed adjacent the table 24 of the DXA system 10. The camera 120 is connected to the controller 22 and is operable to obtain a visual image of the table 24 and the location of the positioning of the patient 12 on the table 24. These images from the camera 120 can be employed by the controller 22 to determine the FOV 102 for the DXA system 10. With the information from the camera 120 for the FOV 120, the controller 22 can determine various structural and/or anatomical landmarks 124 of the object/patient 12 relative to the FOV 102 in known manners employed using artificial intelligence ("AI") and/or computer vision system tools. Those landmarks 124 can subsequently be employed by the controller 22 to determine an initial scan starting point 122 to provide sweep images 100 of the desired area of the patient 12. Further, the landmarks 124 can be employed by the controller 22 similar to landmarks 112 for the determination of the offset 114 for alignment of the sweep images 100 of the object/patient 12. These landmarks 124 can additionally be obtained via sources other than a camera 120, such as pressure sensitive pad or capacitive panel or matrix (not shown) disposed on the table 24 which is contacted by the patient 12. Using the determined actual location of the landmarks 124, i.e., the position of the patient 12, from the information obtained from the pad or panel relative to the actual FOV 102, the controller 22 can determine the scan area 116 within which the sweep images 100 are to be obtained for the desired area of the patient 12.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:
1. A method for automatically aligning images obtained while performing a DXA imaging procedure of an object, the method comprising the steps of:
 a. providing a DXA imaging system comprising:
  i. a support on which an object to be imaged is adapted to be positioned;
  ii. a radiation source movably disposed relative to the support and configured to emit radiation beams towards the object;
  iii. a detector movably disposed relative to the support and aligned with the radiation source to receive the radiation beams from the radiation source and generate image data;
  iv. a controller operably connected to the radiation source and the detector to control the movement and operation of the radiation source and detector, the controller configured to receive and process image data from the detector;
  v. a display operably connected to the controller for presenting information to a user; and
  vi. a user interface operably connected to the controller to enable user input to the controller
 b. positioning the object on the support;
 c. operating the radiation source and the detector to obtain at least one image of the object;
 d. determining an offset of the at least one image relative to an image reference; and
 e. aligning the at least one image with the image reference.

2. The method of claim 1, wherein the step of aligning the at least one image with the image reference comprises applying the offset to the at least one image.

3. The method of claim 2, wherein the step of applying the offset to the at least one image comprises shifting the location of the at least one image with regard to a field of view of the DXA imaging system.

4. The method of claim 2, further comprising the step of applying the offset to subsequent images obtained by the DXA imaging system to align the subsequent images with the image reference.

5. The method of claim 4, wherein the step of applying the offset to subsequent images obtained by the DXA imaging system comprises shifting the location of the subsequent images with regard to a field of view of the DXA imaging system.

6. The method of claim 1, wherein the image reference is a geometric representation of the field of view of the DXA imaging system.

7. The method of claim 1, wherein the image reference is a generalized representation of the shape of the object.

8. The method of claim 1, wherein the image reference is a prior scan image of the object.

9. The method of claim 8, wherein the object is at least a portion of a body of a patient.

10. The method of claim 9, wherein the step of determining the offset comprises the steps of:
 a. locating at least one landmark in the at least one image;
 b. comparing the location of the at least one landmark in the at least one image to a position of the same landmark in the prior scan image; and
 c. determining the difference between the location of the landmark in the at least one image and the position of the landmark in the prior scan image to define the offset.

11. The method of claim 9, wherein the step of determining the offset comprises the steps of:
 a. locating at least one landmark in the at least one image;
 b. comparing the location of the at least one landmark in the at least one image to a position of the same landmark in a generalized representation of the shape of the object; and
 c. determining the difference between the location of the landmark in the at least one image and the position of the landmark in the generalized representation to define the offset.

12. The method of claim 1, wherein the step of determining the offset of the at least one image relative to an image reference comprises the steps of:
 a. locating at least one landmark in the at least one image;
 b. comparing the location of the at least one landmark in the at least one image to a position of the same landmark in the reference image;
 c. determining if a desired area of the object to be imaged is outside of a field of view of the DXA imaging system such that no offset can be determined; and
 d. aborting the operation of the radiation source.

13. The method of claim 1, further comprising the steps of:
 a. operating an optical camera connected to the controller to obtain a visual representation of a position of the object on the support after positioning the object on the support;
 b. determining structural landmarks for the object relative to the field of view for the D×A system; and
 c. determining a start point for the operation of the radiation source to obtain the at least one image of the object.

14. The method of claim 1, wherein the wherein the steps of determining the offset of the least one image relative to the image reference and aligning the at least one image with the image reference occur in real time with respect to the step of operating the radiation source and the detector to obtain at least one image of the object.

15. The method of claim 14, further comprising the step of applying the offset to subsequent images obtained by the DXA imaging system to align the subsequent images with the image reference in real time with respect to the step of obtaining the subsequent images by the D×A system.

16. A DXA imaging system comprising:
   a. a support on which an object to be imaged is adapted to be positioned;
   b. a radiation source movably disposed relative to the support and configured to emit radiation beams towards the object;
   c. a detector movably disposed relative to the support and aligned with the radiation source to receive the radiation beams from the radiation source and generate image data;
   d. a controller operably connected to the radiation source and the detector to control the movement and operation of the radiation source and detector, the controller configured to receive and process image data from the detector to obtain at least one image of the object;
   e. a display operably connected to the controller for presenting information to a user; and
   f. a user interface operably connected to the controller to enable user input to the controller wherein the controller is configured to determine an offset for the at least one image relative to an image reference and to align the at least one image with the image reference.

17. The DXA imaging system of claim 16, further comprising an optical camera operably connected to the controller, wherein the controller is configured to determine an initial scan start point from a visual image provided by the camera.

18. The imaging system of claim 16, wherein the image reference is selected from: a geometric representation of a field of view of the DXA imaging system, a generalized representation of the shape of the object, or a prior scan image of the object.

* * * * *